US010149946B2

(12) United States Patent
Bernert

(10) Patent No.: US 10,149,946 B2
(45) Date of Patent: Dec. 11, 2018

(54) ASSEMBLY FOR A DRUG DELIVERY DEVICE AND DRUG DELIVERY DEVICE

(71) Applicant: SANOFI-AVENTIS DEUTSCHLAND GMBH, Frankfurt am Main (DE)

(72) Inventor: Andreas Bernert, Bad Homburg v.d. Hohe (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 14/786,800

(22) PCT Filed: May 8, 2014

(86) PCT No.: PCT/EP2014/059403
§ 371 (c)(1),
(2) Date: Oct. 23, 2015

(87) PCT Pub. No.: WO2014/184080
PCT Pub. Date: Nov. 20, 2014

(65) Prior Publication Data
US 2016/0074589 A1    Mar. 17, 2016

(30) Foreign Application Priority Data

May 16, 2013    (EP) .................................... 13167953

(51) Int. Cl.
*A61M 5/20*    (2006.01)
*A61M 5/315*    (2006.01)
*A61M 5/24*    (2006.01)

(52) U.S. Cl.
CPC .......... *A61M 5/31543* (2013.01); *A61M 5/20* (2013.01); *A61M 5/24* (2013.01);
(Continued)

(58) Field of Classification Search
CPC .......... A61M 5/31543; A61M 5/31553; A61M 5/31583; A61M 5/31535; A61M 5/31541
See application file for complete search history.

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| CN | 101107031 | 1/2008 |
| EP | 0937471 | 8/1999 |

(Continued)

OTHER PUBLICATIONS

International Search Report for Int. App. No. PCT/EP2014/059403, completed Jul. 28, 2014.

*Primary Examiner* — Andrew Gilbert
*Assistant Examiner* — Dung Ulsh
(74) *Attorney, Agent, or Firm* — Fish & Richardson P.C.

(57) ABSTRACT

An assembly for use in a drug delivery device includes a cartridge, a housing and a cartridge holder. The cartridge holder is releasably attached to the housing. The assembly includes a piston rod configured to move from a start position to an end position to dispense a dose of medication when the cartridge holder is attached to the housing, and the piston rod is configured to be reset to the start position when the cartridge holder is detached from the housing. The assembly further comprises a flexible element configured to axially fix the cartridge in the cartridge holder when the cartridge holder is attached to the housing. Furthermore, the assembly comprises a guiding element in threaded engagement with the piston rod. The flexible element is configured
(Continued)

to fix the guiding element with respect to a housing of the drug delivery device when the cartridge holder is attached to the housing.

16 Claims, 3 Drawing Sheets

(52) U.S. Cl.
CPC .... *A61M 5/31553* (2013.01); *A61M 5/31583* (2013.01); *A61M 5/31535* (2013.01); *A61M 5/31541* (2013.01); *A61M 2005/2477* (2013.01); *A61M 2205/581* (2013.01)

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1* | 12/2004 | Veasey | A61M 5/24 604/208 |
| 2005/0113765 A1 | 5/2005 | Veasey et al. | |
| 2006/0153693 A1 | 7/2006 | Fiechter et al. | |
| 2007/0021718 A1* | 1/2007 | Burren | A61M 5/24 604/110 |
| 2008/0306446 A1* | 12/2008 | Markussen | A61M 5/20 604/139 |
| 2009/0275916 A1 | 11/2009 | Harms et al. | |
| 2010/0114025 A1* | 5/2010 | Moller | A61M 5/20 604/135 |
| 2010/0168677 A1* | 7/2010 | Gabriel | A61M 5/31551 604/189 |
| 2011/0077595 A1* | 3/2011 | Eich | A61M 5/31501 604/135 |
| 2012/0004620 A1* | 1/2012 | Spool | A61M 5/24 604/211 |
| 2013/0006193 A1* | 1/2013 | Veasey | A61M 5/31543 604/211 |
| 2014/0046268 A1* | 2/2014 | Quinn | A61M 5/31541 604/209 |
| 2015/0080811 A1* | 3/2015 | Wieselblad | A61M 5/3155 604/207 |
| 2016/0074589 A1* | 3/2016 | Bernert | A61M 5/20 604/211 |

FOREIGN PATENT DOCUMENTS

| | | |
|---|---|---|
| EP | 0937476 | 8/1999 |
| JP | 2009-502273 | 1/2009 |
| WO | 99/38554 | 8/1999 |
| WO | 01/10484 | 2/2001 |
| WO | WO 2006/076921 | 7/2006 |
| WO | WO 2007/017052 | 2/2007 |
| WO | 2010/043533 | 4/2010 |
| WO | WO 2012/062718 | 5/2012 |
| WO | 2012/152666 | 11/2012 |

* cited by examiner

ASSEMBLY FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. § 371 of International Application No. PCT/EP2014/059403 filed May 8, 2014, which claims priority to European Patent Application No. 13167953.2 filed May 16, 2013. The entire disclosure contents of these applications are herewith incorporated by reference into the present application.

TECHNICAL FIELD

The present disclosure relates to an assembly for a drug delivery device. In particular, the disclosure relates to pen-type drug delivery devices.

BACKGROUND

Pen-type drug delivery devices are used for injections by persons without formal medical training. This is increasingly common for self-treatment among patients having diabetes or the like. Such self-treatment enables patients to effectively manage their disease. Pen type drug delivery devices usually comprise a housing in which a drive mechanism is located. Some kinds of drug delivery devices also comprise a compartment to accommodate a cartridge in which the drug is contained. By means of the drive mechanism, a piston in the cartridge is displaced such that the drug accommodated therein is dispensed through a needle.

Prior to injection, the required dose of a drug is set by means of a dose setting mechanism. Common designs of dose setting mechanisms comprise a number of tubular or sleeve-like elements such as a dose dial sleeve, a dose indicating sleeve, a drive sleeve or a ratchet sleeve. Such sleeves are often accommodated within and connected to each other.

Some devices may be reused when a full amount of medication has been delivered from the drug delivery device.

SUMMARY

It is an object of the present invention to provide an assembly for a drug delivery device having improved properties.

Document US 2010/0114025 A1 refers to a reusable injection device.

According to one aspect of the invention, an assembly for use in a drug delivery device is provided. The assembly comprises a cartridge, a housing and a cartridge holder. The cartridge holder is releasably attached to the housing. The assembly further comprises a piston rod which is configured to be moved from a start position to an end position in order to dispense a dose of medication when the cartridge holder is attached to the housing. The piston rod is configured to be reset to the start position when the cartridge holder is detached from the housing. The assembly further comprises a flexible element, wherein the flexible element is configured to axially fix the cartridge in the cartridge holder when the cartridge holder is attached to the housing. The assembly further comprises a guiding element which is in threaded engagement with the piston rod, wherein the flexible element is configured to fix the guiding element with respect to a housing of the drug delivery device when the cartridge holder is attached to the housing.

The advantage of an assembly comprising a flexible element is that tolerances of the components of the assembly may be compensated. Such tolerances may be for example dimensional tolerances due to production techniques. For example, tolerances of the cartridge may be compensated.

The cartridge may be tensioned towards a distal end of the device by means of the flexible element when the cartridge holder is attached to the housing. Thereby, the cartridge may be axially fixed with respect to the cartridge holder. Thereby, an unintended movement of the cartridge in the cartridge holder is inhibited. Thereby, the dosing accuracy may be increased. The use of a flexible element is particularly advantageous in a reusable device. Furthermore, the flexible element may be configured to inhibit an axial movement of the guiding element when the cartridge holder is attached to the housing. The flexible element may act as a fixing element. For example, the flexible element may force the guiding element into an engagement with the housing, such that a movement of the guiding element is inhibited. Thereby, the dosing accuracy of the device may be improved.

The term "distal end" may mean an end of the assembly or of any component of the assembly which is nearest to a dispensing end of the device. The term "proximal end" may mean an end of the assembly or of any component of the assembly which is furthest away from the dispensing end of the device.

When the drug delivery device is in an assembled state, the flexible element may be clamped between the cartridge and the guiding element. In particular, a distal face of the flexible element may be in contact with the cartridge, and a proximal face of the flexible element may be in contact with the guiding element. The distal face may be directed towards the dispensing end of the device, and the proximal end may be directed away from a dispensing end of the device.

The piston rod may be configured as a lead screw. In particular, the piston rod may be rotated from its start position towards its end position during the dispensing of a dose. The start position may be a most proximal position of the piston rod. The end position may be a most distal position of the piston rod. During the setting of a dose, the piston rod may be fixed with respect to the housing. During a reset of the piston rod, the piston rod may be rotated from its end position towards its start position. In order to cause a movement of the piston rod towards its end position, an axial force needs to be exerted on the distal end of the piston rod, which is directed in a proximal direction. A rotation of the piston rod during the reset may be achieved due to the threaded engagement of the piston rod and the guiding element. The guiding element may be a thread nut. In particular, when an axial force is exerted on the piston rod and an axial movement of the guiding element is restricted, the piston rod is caused to rotate. Thereby, an axial movement of the piston rod is achieved. In particular, the pitch of the thread of the guiding element may be such that the piston rod is caused to rotate when an axial force is exerted on the piston rod. During the dispensing of a dose, the piston rod may rotate through the guiding element towards a distal end of the device.

According to one embodiment, the flexible element may be a spring. For example, the flexible element may be a flat spring or a spring washer. Alternatively, the flexible element may be any other kind of spring element which is suited to be inserted into a drug delivery device.

According to one embodiment, the flexible element may be fixed to the guiding element. Thereby, the flexible element may be inhibited from disengaging from the assembly when the cartridge holder is detached from the housing. In one embodiment, the flexible element may be snapped to the guiding element. For example, the flexible element may comprise hooks which may engage with the guiding element. Alternatively, the flexible element may be an integral part of the guiding element. According to a further embodiment, the flexible element may be fixed to the housing. Preferably, the flexible element comprises protrusions which are engaged with corresponding grooves of the housing. Thereby, the flexible element may be enabled to axially move with respect to the housing by a short distance, but may be inhibited from disengaging from the assembly.

When the drug delivery device is in a disassembled state, in particular when the cartridge holder is detached from the housing, the flexible element does not fix the guiding element with respect to the housing anymore. In particular, the guiding element may be enabled to move axially with respect to the housing. Thereby, the guiding element may be released from the housing. For example, the guiding element may be enabled to rotate when it is released from the housing. During a reset of the piston rod, the guiding element may be forced into engagement with the housing again. Thereby, a rotation of the piston rod may be enabled during the reset operation.

According to one embodiment, the assembly comprises a drive element. The drive element may be configured to cause a movement of the piston rod in a distal direction. In particular, a rotation of the drive member may cause a rotational and axial movement of the piston rod during the dispensing of a dose. In particular, when the piston rod is rotated due to a rotation of the drive element, the piston rod is caused to axially move as a result of its cooperation with the guiding element. The drive element may be engaged with the piston rod. For example, the drive element may comprise splines, which are engaged with corresponding grooves of the piston rod. The grooves may extend along the entire length of the piston rod. In particular, the drive element may be axially moveable with respect to the piston rod. Furthermore, the drive element may be rotationally fixed with respect to the piston rod.

According to one embodiment, the assembly may comprise a locking member. The locking member may be fixed with respect to the housing during the setting of a dose. In particular, the locking member and the housing may comprise corresponding engagement means. The corresponding engagement means may be engaged during the setting of a dose. During the dispensing of a dose, the locking member may be configured to rotate with respect to the housing. The rotation of the locking member may cause the piston rod to move in a distal direction when the drug delivery device is in an assembled state. In order to enable a rotation of the locking member, the locking member has to be disengaged from the housing. In particular, the locking member may be configured to move axially with respect to the housing during the dispensing of a dose. Thereby, the engagement means of the locking member disengage from the engagement means of the housing, and the locking member may be enabled to rotate.

The drive element may be fixedly coupled to the locking member such that the drive element may be fixed with respect to the housing by means of the locking member at least during the setting of a dose. The drive element and the locking member may be fixed with respect to each other such that a movement of the locking member causes a corresponding movement of the drive element. The locking member may be connected to the piston rod by means of the drive member.

According to one embodiment, the assembly comprises a spring member. The spring member may be a torsion spring. The spring member may be loaded during the setting of a dose. During the dispensing of a dose, energy may be released from the spring member. Thereby, the piston rod may be moved towards its end position. According to one embodiment, a relaxation of the spring member may cause a rotation of the locking member at least during the dispensing of a dose.

According to one embodiment, the assembly comprises an actuator which is configured to be operated in order to dispense a dose of medication. The actuator may be a button. The spring member may be enabled to relax when the actuator is operated.

During the reset of the piston rod, the locking member may be configured to inhibit an unintentional relaxation of the spring member. Thereby, an unintentional movement of the piston rod towards the end position may be inhibited during a reset of the piston rod. In particular, during the reset of the piston rod, a rotation of the locking member in one direction is allowed, and a rotation in an opposite direction is inhibited. In particular, the locking member is allowed to rotate such that the spring member is pre-tensioned. Thereby, the torque of the spring member during the dispensing of a dose may be sufficient to drive the piston rod.

According to one embodiment, the assembly may comprise a rotation member. The rotation member may be rotated during the setting and during the dispensing of a dose. During the setting of a dose, the rotation member may be rotated in a dose setting direction, for example in a clockwise direction. During the dispensing of a dose, the rotation member may be rotated in a dose dispensing direction, for example an anticlockwise direction. The locking member may be coupled to the rotation member. When the actuator is actuated, the rotation member may be moved in an axial direction. Thereby, the rotation member may move the locking member out of its engagement with the housing. Furthermore, a rotation of the rotation member may cause a rotation of the locking member during the dispensing of a dose.

One end of the spring member may be fixedly coupled to the rotation member. The other end of the spring member may be fixedly coupled to the housing or to another part which is fixed with respect to the housing. When the rotation member is rotated in a dose setting direction, the spring member may be wound up. Thereby, energy may be stored in the spring member. During the reset of the piston rod, the rotation member may be rotated in a dose setting direction in order to pre-tension the spring member.

The assembly may comprise a dose setting member which is configured to be rotated in a dose setting direction in order to set a dose. The rotation member may be rotated when a user rotates the dose setting member.

The rotation member may comprise a ratchet mechanism. The ratchet mechanism may comprise a ratchet arm. The rotation member may be coupled with respect to the locking member by means of the ratchet mechanism. The ratchet mechanism may allow a rotation of the rotation member in a dose setting direction with respect to the locking member. An unintended rotation of the rotation member in a dose dispensing direction may be inhibited during the setting of a dose by means of the ratchet mechanism.

According to one embodiment, the assembly may comprise a drive shaft. The drive shaft may be coupled to the dose setting member by means of splines, which engage with corresponding grooves of the dose setting member. The rotation member may be coupled to the dose setting member by means of the drive shaft. During the dispensing of a dose, the drive shaft may be disengaged from the dose setting member.

Furthermore, a drug delivery device is provided, the drug delivery device comprising a drive assembly. The drive assembly may be configured as previously described.

The drug delivery device may be an injection device, in particular a pen-type device. The drug delivery device may be suited to deliver a dose of medication to a user. A dose may be delivered by depressing the actuator. The drug delivery device may be a variable dose device such that a user can select the size of a dose. In particular, a user may select the size of a dose by rotating the dose setting member. The drug delivery device may be configured for multiple dose applications. The medication may be delivered to a user by means of a needle. The device may be delivered to a user in a fully assembled condition ready for use. In particular, the device may be prefilled. The drug delivery device may be a reusable device. The term "reusable" means that the drug delivery device can be reused after an available amount of medication has been delivered from a cartridge which is located in the drug delivery device. The drug delivery device may be configured to deliver a liquid medication. The medication may be, for example, insulin.

The term "medication", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further features, refinements and expediencies become apparent from the following description of the exemplary embodiments in connection with the figures.

DETAILED DESCRIPTION

Figure 1:
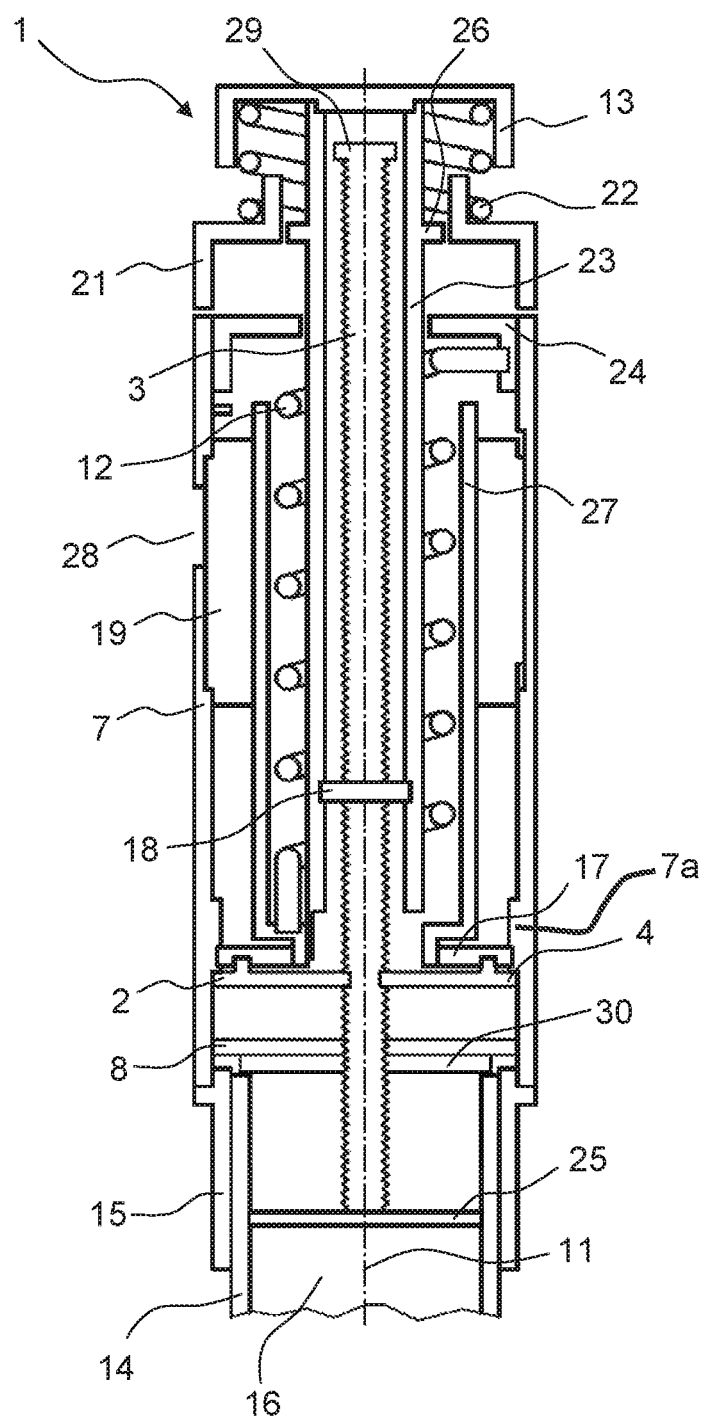
FIG. 1 shows a drug delivery device.

FIG. 1 shows a drug delivery device 1 comprising an assembly 2. In particular, FIG. 1 shows the drug delivery device 1 in a state when it is not being operated, i. e. when no dose of medication is delivered from the device.

The assembly 2 comprises a piston rod 3, which is configured to be moved in a distal direction in order to dispense a dose of medication. In particular, the piston rod 3 is configured to move a piston 16 which is arranged in a cartridge 14 towards the dispensing end of the drug delivery device 1. In particular, the piston rod 3 comprises a bearing 25, wherein the bearing 25 is in contact with the piston 16. The cartridge is arranged in a cartridge holder 15, which is connected to a housing 7. The piston rod 3 is configured as a lead screw.

In order to set a dose of medication, the assembly 2 comprises a dose setting member 21. The dose setting member 21 may be rotated by a user. In particular, the dose setting member 21 is axially fixed, but rotationally moveable with respect to the housing 7. In particular, the length of the drug delivery device 1 does not change during a rotation of the dose setting member 21. The assembly further comprises a drive shaft 23. By rotating the dose setting member 21, the drive shaft 23 is also rotated. In particular, the drive shaft 23 may be rotationally fixed with respect to the dose setting member 21 during the setting of a dose by means of splines 26. The splines 26 may engage with corresponding grooves (not shown) of the dose setting member 21.

The assembly 2 furthermore comprises a rotation member 27. The rotation member 27 is configured as a sleeve. The rotation member 27 is arranged concentrically around the drive shaft 21. The rotation member 27 may be fixed to the drive shaft 23 by a snap connection. The rotation member 27 is axially fixed with respect to the drive shaft 23. For assembly reasons, the drive shaft 23 and the rotation member 27 are designed as separate parts. In an alternative embodiment, the drive shaft 23 and the rotation member 27 may be designed as one part. Rotating the drive shaft 23 in a dose setting direction also rotates the rotation member 27. The dose setting direction may be a clockwise direction.

The assembly 2 comprises a spring member 12. The spring member 12 may be a torsion spring. One end of the spring member 12 is fixed to a zero stop 24, which will be described later. In an alternative embodiment, one end of the spring member 12 may be fixed to the housing 7. The other end of the spring member 12 is fixed to the rotation member 27. When the rotation member 27 is rotated during the setting of a dose, the spring member 12 is wound up, such that energy is stored in the spring member 12.

The assembly 2 further comprises an indicator 19. The indicator 19 may be a sleeve member, for example a number sleeve. The indicator 19 is configured to indicate the amount of a set dose to a user. For example, the amount of a set dose may be shown through a window 28 in the housing 7 of the drug delivery device 1. The indicator 19 is rotationally fixed, but axially moveable with respect to the rotation member 27. For example, the indicator 19 may comprise splines at its inner circumference which may engage with corresponding grooves of the rotation member 27. In particular, the indicator 19 is arranged concentrically around the rotation member 27. Furthermore, the indicator 19 is in threaded engagement with the housing 7. During the setting of a dose, the indicator 19 is rotated by the rotation member 27 in the dose setting direction. Thereby, the indicator 19 is forced to move in a distal direction because of its threaded engagement with the housing 7. In order to cancel a set dose, the dose setting member 21 may be rotated in a dose cancelling direction. The dose cancelling direction may be the anti-clockwise direction.

The assembly 2 further comprises a locking member 17. The locking member 17 is rotationally fixed with respect to the housing 7 during the setting of a dose. For example, the locking member 17 comprises splines which engage with corresponding grooves 7a of the housing 7. On an inner circumference of the locking member 17, a set of teeth (not shown) is arranged. The rotation member 27 is engaged with the set of teeth of the locking member 17 by means of at least one ratchet arm (not shown). In particular, the locking member 17 and the rotation member 27 are engaged such that the rotation of the rotation member 27 in a dose setting direction is allowed during the setting of a dose, and an unintended rotation of the rotation member 27 in a dose cancelling direction is inhibited. Thereby, it is inhibited that the torque from the spring member 12 rotates the rotation member 27 in a dose cancelling direction when a user releases the dose setting member 21. During the setting of a dose, the at least one ratchet arm of the rotation member 27 is moved over the teeth of the locking member 17. Thereby, an audible click may be produced with each unit set.

In order to cancel a set dose, a user rotates the dose setting member 21 in a dose cancelling direction. During the cancelling of a dose, the drive shaft 23 may rotate relative to the rotation member 27 by a short distance. Thereby, a feature, for example a protrusion of the drive shaft 23, slides over the at least one ratchet arm of the rotation member 27. Thereby, the at least one ratchet arm of the rotation member 27 is pressed in a radial inward direction. Thereby, the engagement between the rotation member 27 and the locking member 17 is temporarily released, such that the rotation member 27 may be rotated in a dose cancelling direction.

A last dose member 18 is arranged between the piston rod 3 and the drive shaft 23. The last dose member 18 may be a last dose nut. The last dose member 18 is in threaded engagement with the piston rod 3. Furthermore, the last dose member 18 is engaged with the drive shaft 23 by means of external ribs which engage with corresponding grooves inside the drive shaft 23. In particular, the last dose member 18 is rotationally fixed but axially moveable with respect to the drive shaft 23. When the drive shaft 23 rotates, for example during the setting of a dose, the last dose member 18 is rotated by the drive shaft 23. Thereby, the last dose member 18 moves along the piston rod. When a last dose is selected, the last dose member 18 abuts a stop feature 29. The stop feature 29 is arranged at a proximal end of the piston rod 3. When the last dose member 18 abuts the stop feature 29, the further setting of a dose is inhibited. In particular, the last dose member 18 inhibits the setting of a dose which exceeds the amount of remaining medicament in the cartridge 14.

In order to dispense a dose of medication, the actuator 13 has to be actuated by a user.

Figure 2:
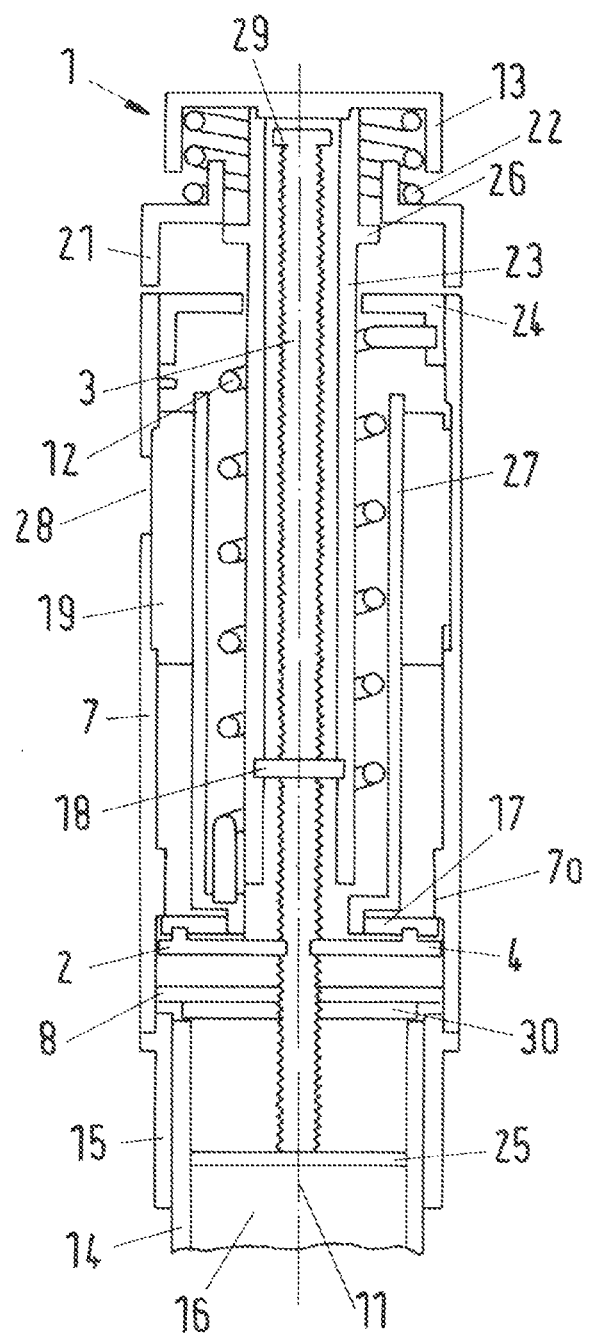
FIG. 2 shows the drug delivery device of FIG. 1 in a dispensing step with the locking member disengaged from the housing.

When the actuator 13 is actuated, in particular moved in a distal direction, the drive shaft 23 is also moved in a distal direction. Thereby, the drive shaft 23 is disengaged from the dose setting member 21. When the drive shaft 23 is moved in a distal direction, the rotation member 27 and the locking member 17 are also moved in a distal direction together with the drive shaft 23. Thereby, the locking member 17 is disengaged from its engagement with the grooves 7a of the housing 7 as illustrated in FIG. 2. In particular, the locking member 17 is allowed to rotate with respect to the housing 7 when the actuator 13 is actuated by a user. When the locking member 17 is enabled to rotate with respect to the housing 7, the energy which is stored in the spring member 12 may be released. In particular, the spring member 12 exerts a torque on the rotation member 27, such that the rotation member 27 is rotated during the dispensing of a dose. A rotation of the rotation member 27 during the dispensing of a dose also rotates the locking member 17.

The assembly 2 comprises a drive element 4. The drive element 4 is configured as a spline nut. The drive element 4 is connected to the locking member 17. In particular, the drive element 4 is rotationally and axially fixed with respect to the locking member 17. Thereby, the drive element 4 rotates during the dispensing of a dose. Furthermore, the drive element 4 is engaged with the piston rod 3. In particular, the drive element 4 comprises splines, which are engaged with axial grooves of the piston rod 3. Thereby, the drive element 4 is rotationally fixed but axially moveable with respect to the piston rod 3.

The drive element 4 may comprise a feedback feature (not shown). For example, at the outer circumference of the drive element 4, at least one, for example two, clicker arms, may be arranged. When the drive element 4 rotates during the dispensing of a dose, the clicker arms may move over teeth in the housing 7, thereby creating an audible feedback. The feedback may indicate to a user that a dose is currently being dispensed. Accordingly, an end of the audible feedback indicates to a user that a complete dose has been dispensed.

The assembly 2 further comprises a guiding element 8. The guiding element 8 is configured as a thread nut. The guiding element 8 is in threaded engagement with the piston rod 3. The guiding element 8 is fixed with respect to the housing 7 of the drug delivery device 1. When the drive element 4 rotates during the dispensing of a dose, the piston rod 3 is also rotated. Due to the threaded engagement between the piston rod 3 and the guiding element 8, the rotation of the piston rod 3 causes the piston rod 3 to move in a distal direction. Thereby, the piston 16 is moved in a distal direction and thereby a dose is dispensed. During the dispensing of a dose, the indicator 19 is rotated back to its initial position. In particular, during the dispensing of a dose, the indicator 19 performs a combined rotational and axial movement towards a proximal end of the device, until the indicator 19 abuts a zero stop 24. The zero stop 24 is rigidly fixed to the housing 7. When the indicator 19 abuts the zero stop 24, a further rotation of the rotation member 27 in a dose dispensing direction due to the torque of the spring member 12 is inhibited. Thereby, a further dispensing of a dose is inhibited.

When a user releases the actuator 13, a reset spring 22, which is arranged between the actuator and the dose setting member 21, moves the actuator back to its initial position. Thereby, the drive shaft 23 is moved in a proximal direction together with the actuator 13. Thereby, the drive shaft 23 reengages with the dose setting member 21.

The assembly 2 comprises a flexible element 30. The flexible element 30 may be, for example, a flat spring. The flexible element 30 is in contact with the cartridge 14 when the drug delivery device is in an assembled state, as shown in FIG. 1. In particular, the flexible element 30 exerts a force on the cartridge 14 such that the cartridge is biased towards the distal end of the device. Thereby, the flexible element 30 axially constrains the cartridge 14. Thereby, the flexible element 30 serves to compensate tolerances of the cartridge 14. Thereby, the dosing accuracy of the device is increased.

The flexible element 30 is arranged between the cartridge 14 and the guiding element 8 when the drug delivery device is in an assembled state. In particular, the flexible element 30 exerts a force on the guiding element 8 such that the guiding element is biased towards a proximal end of the device. Thereby, the guiding element 8 is held in engagement with engagement means (not shown) of the housing 7. Thereby, the guiding element 8 is rotationally and axially fixed with respect to the housing 7. When the cartridge holder 15 is disengaged from the housing 7, the guiding element 8 is allowed to move out of the engagement with the housing 7. Thereby, the guiding element 8 may rotate with respect to the housing 7.

When the last dose has been set and the cartridge 14 is empty, a new cartridge may be inserted into the drug delivery device. In particular, the cartridge holder 15 may be detached from the housing 7. In order to reuse the drug delivery device, the piston rod 3 and the last dose member 18 both need to be reset to their start positions. The start position may be a most proximal position of the piston rod 3. In particular, the piston rod 3 and the last dose member 18 are rotated back to their start positions. For example, the piston rod 3 and the last dose member 18 may be rotated to their start positions by the presence of a new cartridge 14 within the cartridge holder 15 or by pushing the piston rod 3 by hand or on a flat surface like a table. After moving the piston rod 3 and the last dose member 18 back to their start position, the cartridge holder 15 holding a new cartridge 14 may be mounted on the housing 7. The cartridge holder 15 may be attached to the housing 7 for example by a bayonet or a threaded connection between the cartridge holder 15 and the housing 7.

When the cartridge holder 14 is detached from the housing 7, the flexible element 30 is inhibited from being removed from the assembly 2. According to one embodiment, the flexible element 30 may be fastened to the guiding element 8, for example by means of hooks which engage with corresponding engagement features of the guiding element 8. Alternatively, the flexible element 30 may be an integral element of the guiding element 8. Alternatively, the flexible element 30 may be engaged with the housing 7 by means of hooks.

When the piston rod 3 pushed towards the proximal end of the device, in particular towards its start position, the guiding element 8 is moved towards the proximal end together with the piston rod 3 and thereby reengages with the housing 7. Thereby, the guiding element 8 is axially and rotationally fixed with respect to the housing 7 again. A further axial movement of the piston rod 3 forces the piston rod 3 to rotate, due to its engagement with the guiding element 8. In an alternative embodiment, the guiding element 8 may be permanently fixed with respect to the housing 7.

When the piston rod 3 rotates during the reset of the piston rod 3, the drive element 4 and the last dose member 18 are also rotated, due to the engagement of the drive element 4 with the piston rod 3 and the last dose member 18 with the piston rod 3. Since the locking member 17 is fixedly coupled with the drive element 4, the locking member 17 is also rotated. The rotation of the locking member 17 rotates the rotation member 27. Thereby, the spring member 12 is wound up such that it is pre-tensioned.

Figure 3:
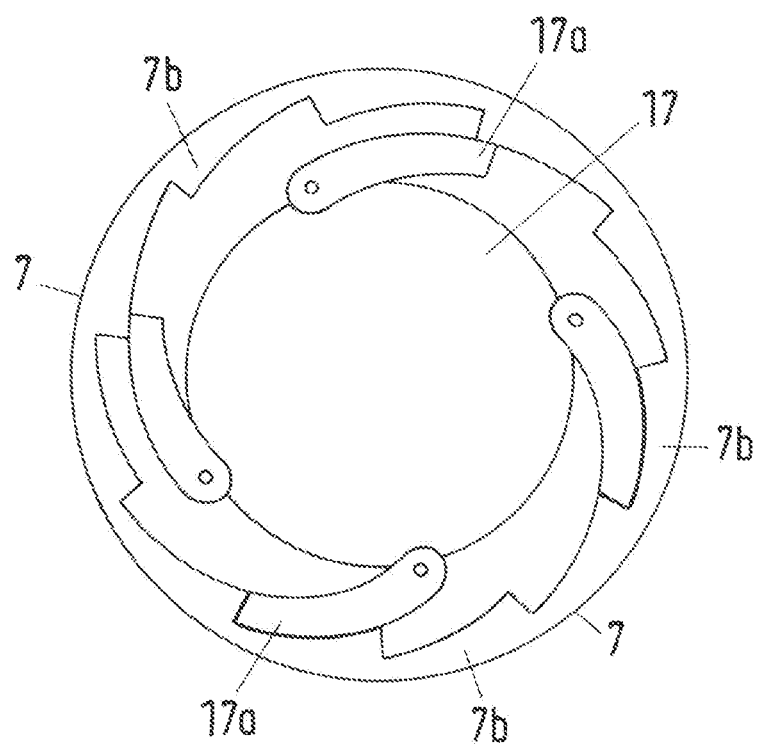
FIG. 3 shows the drug delivery device of FIG. 1 where the locking member is enabled to rotate in one direction during the reset of the piston rod and where rotation of the locking member in an opposite direction is inhibited.

The locking member 17 comprises a further ratchet mechanism as shown in FIG. 3. The ratchet mechanism for example comprises a ratchet arm 17a which interacts with corresponding features, for example teeth 7b, which are located on an inner circumference of the housing. The ratchet mechanism allows a rotation of the locking member 17 in a first direction during the reset of the piston rod 3, but inhibits a rotation of the locking member 17 in an opposed direction. Thereby, an unintended relaxation of the spring member 12 during the reset of the piston rod 3 is inhibited. In particular, the energy which is stored in the spring member 12 after it has been pre-tensioned to a certain degree is not released. Thereby, an unintended rotation of the rotation member 27 in a dose dispensing direction is inhibited. Thereby, an unintended movement of the piston rod 3 away from its start position may be inhibited during the reset of the piston rod 3.

The invention claimed is:

1. An assembly for use in a drug delivery device,
   comprising a cartridge, a housing and a cartridge holder, wherein the cartridge holder is releasably attached to the housing, and
   comprising a piston rod which is configured to be moved from a start position to an end position in order to dispense a dose of medication when the cartridge holder is attached to the housing, and wherein the piston rod is configured to be reset to the start position when the cartridge holder is detached from the housing, and
   comprising a flexible element, wherein the flexible element is configured to axially fix the cartridge in the cartridge holder when the cartridge holder is attached to the housing, and
   further comprising a guiding element which is in threaded engagement with the piston rod, wherein the flexible element is configured to fix the guiding element with respect to a housing of the drug delivery device when the cartridge holder is attached to the housing, and
   further comprising a locking member being fixed with respect to the housing during a setting of a dose and being configured to rotate with respect to the housing during the dispensing of a dose, wherein a rotation of the locking member causes the piston rod to move in a distal direction when the drug delivery device is in an assembled state,
   further comprising a rotation member directly engaged with the locking member, the rotation member being configured to rotate during a setting of a dose, and
   wherein the flexible element is configured to inhibit an axial movement of the guiding element when the cartridge holder is attached to the housing.

2. The assembly according to claim 1, wherein the flexible element is clamped between the cartridge and the guiding element when the drug delivery device is in an assembled state.

3. The assembly according to claim 1, wherein the flexible element is configured as a flat spring.

4. The assembly according to claim 1, wherein the flexible element is fixed to the guiding element.

5. The assembly according to claim 1, wherein the guiding element is released from an engagement with the housing when the drug delivery device is in a disassembled state, thereby being enabled to move axially with respect to the housing.

6. The assembly according to claim 1, wherein the piston rod is configured to rotate through the guiding element during the dispensing of a dose.

7. The assembly according to claim 1, wherein the locking member is configured to move axially during the dispensing of a dose.

8. The assembly according to claim 1, comprising a spring member, wherein a relaxation of the spring member is configured to cause a rotation of the locking member at least during the dispensing of a dose.

9. The assembly according to claim 8, wherein the locking member is configured to inhibit an unintentional relaxation of the spring member during the reset of the piston rod.

10. The assembly according to claim 1, wherein the locking member is enabled to rotate in one direction during the reset of the piston rod, and wherein a rotation of the locking member in an opposite direction is inhibited.

11. The assembly according to claim 1, comprising a drive element, wherein a rotation of the drive element causes a rotational and axial movement of the piston rod during the dispensing of a dose.

12. The assembly according to claim 11, wherein the locking member is connected to the piston rod by means of the drive element.

13. The assembly according to claim 12, wherein the drive element is rotationally fixed and axially moveable with respect to the piston rod.

14. The assembly according to claim 1 comprising a last dose member which is configured to inhibit the setting of a dose which is larger than an amount of a drug remaining in the drug delivery device.

15. The assembly according to claim 1, wherein the flexible element is an integral part of the guiding element.

16. A drug delivery device, comprising an assembly according to claim 1.

* * * * *